United States Patent [19]
Muro et al.

[11] Patent Number: 4,997,834
[45] Date of Patent: Mar. 5, 1991

[54] TRANS-4-AMINO(ALKYL)-1-PYRIDYLCARBAMOYLCYCLOHEXANE COMPOUNDS AND PHARMACEUTICAL USE THEREOF

[75] Inventors: Tomio Muro; Toshio Seki, both of Nakatsu; Masao Abe, Buzen; Jun Inui, Iruma; Hiroyuki Sato, Sayama, all of Japan

[73] Assignee: Yoshitomi Pharmaceutical Industries, Ltd., Osaka, Japan

[21] Appl. No.: 440,374

[22] Filed: Nov. 22, 1989

Related U.S. Application Data

[63] Continuation-in-part of PCT JP88/01189, Nov. 24, 1988

[30] Foreign Application Priority Data

Nov. 24, 1988 [WP] PCT Int'l Appl. ... PCT/JP88/01189

[51] Int. Cl.$^5$ ............................................. C07D 213/64
[52] U.S. Cl. ............................. 514/227.8; 514/235.5; 514/255; 514/318; 514/332; 514/333; 514/335; 514/339; 514/343; 514/352; 544/60; 544/124; 544/360; 546/143; 546/256; 546/261; 546/264; 546/272; 546/275; 546/309; 546/297
[58] Field of Search ............... 546/256, 261, 264, 297, 546/309, 193, 272, 275; 544/60, 124, 360; 514/227.8, 255, 235.5, 318, 339, 349, 332, 352, 333, 335, 343

[56] References Cited

FOREIGN PATENT DOCUMENTS 002920 1/1980 Japan ................................. 546/256

OTHER PUBLICATIONS

Chemical Abstracts, vol. 111, No. 19, Abstract 173,989t, p. 763, Nov. 6, 1989.

Primary Examiner—Mary C. Lee
Assistant Examiner—Zinna Northington Davis
Attorney, Agent, or Firm—Wenderoth, Lind & Ponack

[57] ABSTRACT

A trans-4-amino(alkyl)-1-pyridylcarbamoylcyclohexane compound of the formula:

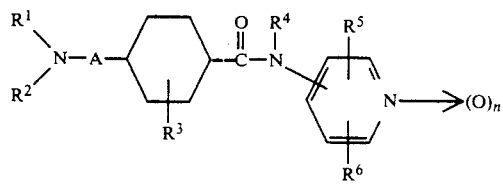

wherein $R^1$ and $R^2$ are the same or different, and respectively represent hydrogen, $C_{1-10}$ alkyl, $C_{2-5}$ alkanoyl, formyl, $C_{1-4}$ alkoxy-carbonyl, amidino, $C_{3-7}$ cycloalkyl, $C_{3-7}$ cycloalkylcarbonyl, phenyl, phenylalkyl, benzoyl, naphthoyl, phenylalkoxycarbonyl, benzylidene, pyridylcarbonyl, piperidyl, pyrrolidylidene or piperidylidene which may be optionally substituted on the ring or $R^1$ and $R^2$ together with the adjacent nitrogen atom form 5 to 6-membered cycle which may have oxygen atom, sulfur atom or optionally substituted nitrogen atom in the cycle, or together with the adjacent nitrogen atom form phthalimido, $R^3$ represents hydrogen or $C_{1-4}$ alkyl, $R^4$ represents hydrogen or $C_{1-4}$ alkyl, $R^5$ represents hydrogen, hydroxy, $C_{1-4}$ alkyl or phenylalkoxy. $R^6$ represents hydrogen or $C_{1-4}$ alkyl, A represents single bond, $C_{1-5}$ straight chain alkylene, or alkylene which is substituted by $C_{1-4}$ alkyl, n represents 0 to 1, an optical isomer thereof and a pharmaceutically acceptable acid addition salt thereof.

These compounds possess antihypertensive activity, and coronary, cerebral and kidney circulation-improving activities and are useful as antihypertensive agents and agents for prevention and treatment of circulatory diseases.

8 Claims, No Drawings

TRANS-4-AMINO(ALKYL)-1-PYRIDYLCARBAMOYLCYCLOHEXANE COMPOUNDS AND PHARMACEUTICAL USE THEREOF

This is a continuation-in-part of PCT/JP88/1189, filed Nov. 24, 1988.

FIELD OF THE INVENTION

The present invention relates to novel and pharmaceutically useful trans-4-amino(alkyl)-1-pyridylcarbamoylcyclohexane compounds, pharmaceutically acceptable acid addition salts thereof and pharmaceutical use thereof.

BACKGROUND OF THE INVENTION

It is known that one of the causes of hypertentions, and coronary or cerebral circulatory diseases, which constitute the severe social problems as adult diseases, is the abnormal construction of smooth muscles and the construction of smooth muscles is caused by increasing the intracellular concentrations of calcium ion. The rise of the intracellular concentrations of calcium ion is caused (1) through the membrane potential-dependent calcium channel, (2) by releasing from the intracellular organella for storage of calcium and (3) through the receptor-dependent channel and so on, and therefore its origin is uneven. Further, it is recognized that the excessive calcium ions induce twitches of the coronary artery and the cerebrovascular and these vascular twitches constitute one of the causes of myocardial infarction, angina pectoris and cerebral infarction.

Then the calcium antagonists have been recently used for the treatment of hypertension, or coronary and cerebral circulatory diseases. However, while the calcium antagonists show antagonistic activity against the membrane potential-dependent calcium channel, scarcely show antagonistic activities against other influx of calcium ion into the cell and liberating calcium ion from the storage organella.

Whereas, in Japanese patent application Unexamined Publication (Kokai) No. 54/1987, there are disclosed N-(o-carboxy or alkoxycarbonyl-substituted phenyl)-trans-4-guanidinomethylcyclohexanecarboxamide derivatives having antiulcer action.

But, it is not known that these compounds possess antihypertensive, and coronary or cerebral circulation-improving activities.

DISCLOSURE OF THE INVENTION

The present inventors conducted intensive studies for the purpose of developing compounds not only having antagonistic activity against the membrane potential-dependent calcium channel which conventional calcium antagonistic agents exhibit but also having antagonistic activity against the intracellular calcium.

As a result, the present inventors have found that trans-4-amino(alkyl)-1-pyridylcarbamoylcyclohexane compounds and pharmaceutically acceptable acid addition salts thereof possess the above-mentioned activities and also antihypertensive activity, and coronary, cerebral and kidney circulation-improving activities and completed the present invention.

Namely, the present invention relates to trans-4-amino-(alkyl)-1-pyridylcarbamoylcyclohexane compounds of the formula:

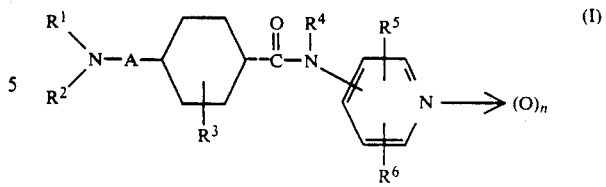

wherein $R^1$ and $R^2$ are the same or different, and respectively represent hydrogen, $C_{1-10}$ alkyl, $C_{2-5}$ alkanoyl, formyl, $C_{1-4}$ alkoxy-carbonyl, amidino, $C_{3-7}$ cycloalkyl, $C_{3-7}$ cycloalkylcarbonyl, phenyl, phenylalkyl, benzoyl, naphthoyl, phenylalkoxy-carbonyl, benzylidene, pyridylcarbonyl, piperidyl, pyrrolidylidene or piperidylidene which may be optionally substituted on the ring or $R^1$ and $R^2$ together with the adjacent nitrogen atom form 5 to 6-membered cycle which may have oxygen atom, sulfur atom or optionally substituted nitrogen atom in the cycle, or together with the adjacent nitrogen atom form phthalimido, $R^3$ represents hydrogen or $C_{1-4}$ alkyl, $R^4$ represents hydrogen or $C_{1-4}$ alkyl, $R^5$ represents hydrogen, hydroxy, $C_{1-4}$ alkyl or phenylalkoxy, $R^6$ represents hydrogen or $C_{1-4}$ alkyl, A represents single bond, $C_{1-5}$ straight chain alkylene, or alkylene which is substituted by $C_{1-4}$ alkyl, n represents 0 to 1, optical isomers thereof and pharmaceutically acceptable acid addition salts thereof.

Moreover, the present invention relates to the agents for the prevention and treatment of the circulatory diseases comprising the compounds of the formula (I) or pharmaceutically acceptable acid addition salts thereof as active ingredients.

In the present specification, $C_{1-10}$ alkyl includes methyl, ethyl, propyl, isopropyl, butyl, isobutyl, tert-butyl, pentyl, hexyl, heptyl, octyl, nonyl or decyl; $C_{2-5}$ alkanoyl includes acetyl, propionyl, isopropionyl, butyryl, isobutyryl, tert-butyryl or valeryl; $C_{1-4}$ alkoxy-carbonyl includes methoxycarbonyl, ethoxycarbonyl, propoxycarbonyl, isopropoxycarbonyl, butoxycarbonyl, isobutoxycarbonyl or tert-butoxycarbonyl; $C_{3-7}$ cycloalkyl means cyclopropyl, cyclobutyl, cyclopentyl, cyclohexyl or cycloheptyl; $C_{3-7}$ cycloalkyl-carbonyl means cyclopropylcarbonyl, cyclobutylcarbonyl, cyclopentylcarbonyl, cyclohexylcarbonyl or cycloheptylcarbonyl; phenylalkyl includes benzyl, phenylethyl, phenylpropyl or phenylbutyl; phenylalkoxycarbonyl includes phenylethoxycarbonyl, phenylpropoxycarbonyl or phenylbutoxycarbonyl; pyridylcarbonyl means 2pyridylcarbonyl, nicotinoyl or isonicotinoyl; piperidyl means 2-piperidyl, 3-piperidyl or 4-piperidyl; pyrrolidylidene means 2-pyrrolidylidene or 3-pyrrolidylidene; piperidylidene means 2piperidylidene, 3-piperidylidene or 4-piperidylidene; 5 or 6-membered cycle formed together with the adjacent nitrogen atom includes pyrrolidinyl, piperidino, piperazinyl, morpholino or thiomorpholino; phenylalkoxy includes benzyloxy, phenylethoxy, phenylpropoxy or phenylbutoxy; $C_{1-5}$ straight chain alkylene means methylene, ethylene, trimethylene, tetramethylene or pentamethylene; alkylene which is substituted by $C_{1-4}$ alkyl includes methylmethylene, methylpropylene, methyltrimethylene, dimethylethylene, ethylethylene or dimethyltrimethylene; $C_{1-4}$ alkyl includes methyl, ethyl, propyl, isopropyl, butyl, isobutyl or tert-butyl.

Moreover, in each symbols of the formula (I), the optical substituents includes halogen such as chlorine, iodine, bromine and fluorine, $C_{1-4}$ alkyl such as methyl, ethyl, propyl, isopropyl, butyl, isobutyl or tert-butyl; $C_{1-4}$ alkoxy such as methoxy, ethoxy, propoxy, isopropoxy, butoxy, isobutoxy or tert-butoxy; phenylalkyl such as benzyl, phenylethyl, phenylpropyl or phenylbutyl; nitro or amino.

The compounds of formula (I) according to the present invention include pharmaceutically acceptable acid addition salts which are formed together with inorganic or organic acid hydrate forms or various solvent forms.

When the compounds of the formula (I) contain asymmetric carbon atoms, there exist optical isomers or the racemates thereof. The present invention includes all of them.

The compounds of formula (I) of the present invention can be prepared by the following method:

METHOD 1

A method which comprises reacting a carboxylic acid compound of the formula:

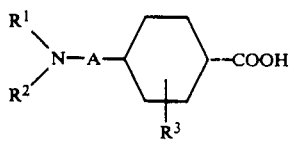
(II)

wherein each symbol is as defined above, or a reactive derivative thereof with an aminopyridine compound of the formula:

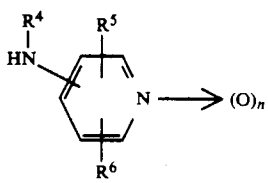
(III)

wherein each symbol is as defined above.

The reactive derivatives of the carboxylic acid compound include an acid halide such as an acid chloride, acid anhydride, a mixed acid anhydride formed with, for example, ethyl chloroformate, an ester such as methyl ester or ethyl ester, a reactive derivative formed with a carbodimide such as dicyclohexylcarbodiimide.

The reaction is carried out in the presence of an inert solvent, usually an organic solvent without a hydroxy group such as tetrahydrofuran, ethyl acetate, benzene, toluene, tetrachloromethane, chloroform, methylene chloride or dimethylformamide. The reaction is carried out at an arbitrary temperature, for example, at −10°-200° C., preferably at 0°-80° C. When the reactive derivatives such as an ester which are not so reactive are used as starting materials, the reaction is carried out at a high reaction temperature.

On the other hand, the reactive derivatives such as a mixed acid anhydride which possess high reactivity, the reaction is carried out at a low reaction temperature.

METHOD 2

The compounds of formula (I) wherein one of $R^1$ and $R^2$ is hydrogen and the other is other than hydrogen, can be prepared by reacting an amine compound of formula:

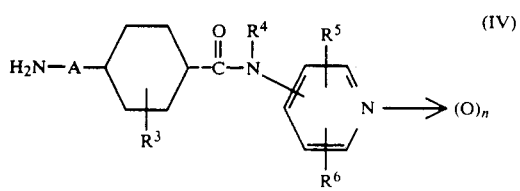
(IV)

wherein each symbol is as defined above, with a carboxylic acid compound or a reactive derivative thereof, a halide compound, an aldehyde compound or a ketone compound.

The carboxylic acid compounds used in this reaction are the compound of formula:

$$R^7\text{—COOH} \qquad (V)$$

wherein $R^7$ is a hydrogen, $C_{1-4}$ alkyl, and $C_{3-7}$ cycloalkyl, phenyl or pyridyl optionally substituted by substituents.

The reactive derivatives thereof include an acid halide, an acid anhydride, a mixed acid anhydride, an ester or a reactive derivative formed with a carbodiimide.

The halide compounds are the compounds of formula:

$$R^8\text{—Hal} \qquad (VI)$$

wherein $R^8$ is $C_{1-10}$ alkyl, and $C_{3-7}$ cycloalkyl or phenyl optionally substituted by substituents; Hal is chlorine, iodine or fluorine, the aldehyde compounds are the compounds of formula:

$$R^9\text{—CHO} \qquad (VII)$$

wherein $R^9$ is hydrogen, $C_{1-9}$ alkyl, or phenyl optionally substituted by substituents, and the ketone compounds are the compounds of formula:

(VIII)

wherein $R^{10}$ and $R^{11}$ are the same or different, and respectively represent $C_{1-9}$ alkyl, or $R^{10}$ and $R^{11}$ together with the adjacent carbonyl group form $C_{3-7}$ cycloalkyl optionally substituted by substituents.

The reaction of the compounds of formula (IV) with the carboxylic acid compounds or the reactive derivatives thereof can be similarly carried out as Method 1. The dehydration reaction of the compounds of formula (IV) with the ketone compounds or the aldehyde compounds, is usually carried out by in a solvent, which is scarcely mixed with water, such as benzene, toluene, xylene, tetrachloromethane, chloroform or dichloromethane. In this reaction, a small amount of an acid such as p-toluenesulfonic acid can be advantageously added.

The objective compound can be also prepared by reducing the alkylidene compounds or the benzylidene compounds optionally substituted by substituents which can be obtained by the dehydrative condensation reaction. The reduction reaction can be usually carried out at −10°-100° C., preferably at 0°-40° C., in an alcohol such as methanol, ethanol or isopropyl alcohol.

The reducing agents include, for example, sodium borohydride, or sodium cyanoborohydride in the presence of a small amount of an acid such as hydrochloric acid, hydrobromic acid or acetic acid. Further, the reduction reaction is carried out by using a catalytic reduction method with Raney-nickel, palladium-carbon or platinic oxide when unaffecting on the other substituents of the objective compounds, and also carried out by subjecting to a reductive amination reaction.

METHOD 3

The compounds of formula (I) wherein $R^1$ and $R^2$ are phenylalkyl or piperidyl optionally substituted by substituents, can be prepared by reducing the compound of formula (I) wherein $R^1$ and $R^2$ are benzylidene or piperidylidene optionally substituted by substituents.

The reduction reaction can be usually carried out at $-10°-100°$ C., preferably $0°-40°$ C. in alcohol such as methanol, ethanol or isopropyl alcohol. Preferably, sodium borohydride is used as a reducing agent. When unaffecting on the other substituents of the objective compounds, the reduction reaction can be also carried out by a catalytic reduction with palladium-carbon or platinic oxide.

METHOD 4

The compounds of formula (I) wherein $R^1$ and $R^2$ together with the adjacent nitrogen form 5 to 6-membered cycle, can be prepared by reacting a compound of the formula:

(IX)

or a compound of the formula:

(X)

wherein Y is oxygen, sulfur or nitrogen optically substituted by substituents, Z is reactive group of an alcohol such as halogen (e.g. chlorine, bromine), sulfonyloxy (e.g. methanesulfonyloxy, p-toluenesulfonyloxy) in the formulae (IX) and (X), with the compound of formula (I) wherein both $R^1$ and $R^2$ are hydrogens.

The reaction can be similarly carried out as Method 2.

METHOD 5

The compounds of formula (I) wherein both $R^1$ and $R^2$ are hydrogens, can be prepared according to the reactions using the following compounds.

(i) Preparation from the compound of formula (I) wherein $R^1$ and $R^2$ are $C_{1-4}$ alkoxy-carbonyl or aralkyloxycarbonyl;

The reaction can be carried out by stirring or allowing to stand at $0°-50°$ C., preferably near $5°-30°$ C., in 3-35%, preferably 15-30% acetic acid in the presence of hydrobromic acid to convert into the compound of formula (I) wherein both $R^1$ and $R^2$ are hydrogens.

In case of the compound of formula (I) wherein $R^1$ and $R^2$ are $C_{1-4}$ alkoxy-carbonyls, the reaction is particularly carried out by stirring and, if nessesary, heating in an inert and suitable organic solvents such as alcohol (e.g. methanol, ethanol, isopropyl alcohol), an ether (e.g. tetrahydrofuran) in the presence of a suitable base such as a hydroxide, a carbonate or a hydrogencarbonate of alkali metal or alkaline earth metal (e.g. sodium hydroxide, potassium carbonate, sodium hydrogencarbonate).

Moreover, in case of the compound of formula (I) wherein $R^1$ and $R^2$ are phenylalkoxycarbonyls, the objective compounds can be also prepared by subjecting to the reductive decomposition reaction with hydrogen, hydrazine, formic acid or ammonium formate as a source of hydrogen in an inert and suitable solvent in the presence of a suitable catalyst such as palladium-carbon.

(ii) Preparation from the compound of formula (I) wherein $R^1$ and $R^2$ together with the adjacent nitrogen atom form phthalimido;

The reaction can be carried out by stirring at $-5°$ C. to room temperature, preferably $0°-5°$ C. in the presence of sodium sulfide hydrate in acetone, tetrahydrofuran or aqueous solvents thereof, by dehydrating the obtained intermediates in the presence of triethylamine in dicyclohexylcarbodiimide or trifluoroacetic acid and followed by stirring at $-20°$ C. with anhydrous hydrazine in tetra hydrofuran to convert into the compound of formula (I) wherein both $R^1$ and $R^2$ are hydrogens. An amino compound can be directly converted from a phthaloyl compound in the presence of a hydrazine in an alcohol.

(iii) Preparation from the compound of formula (I) wherein $R^1$ and $R^2$ are benzylidenes, piperidylidenes or pyrrolidylidenes;

The reaction can be carried out by heating at $30°-60°$ C. under stirring in the presence of a dilute acid solution, in which the other substituents of the objective compound are not influenced, such as 5% hydrochloric acid or 5% sulfuric acid, and also by using an alcoholic solvent.

The compound of formula (I) wherein both $R^1$ and $R^2$ are hydrogens, can be also prepared by reducing the corresponding nitrile compound. The reaction can be carried out by using a reagent, which is not influenced on the other substituents, of the objective compound such as Raney-nickel or hydrazine in accordance with the conventional reduction method.

METHOD 6

The compound of formula (I) wherein $R^1$ is $C_{1-4}$ alkyl or phenylalkyl; $R^2$ is $C_{1-4}$ alkyl, phenyl or phenylalkyl, or $R^1$ and $R^2$ together with the adjacent nitrogen atom form 5 to 6-membered cycle which may have oxygen atom, sulfur atom or optionally substituted nitrogen atom in the cycle and $R^5$ is other than hydroxy, can be prepared by reacting the compound of formula (IV) wherein $R^5$ is other than hydroxy, with sodium nitrite or potassium nitrite in the presence of hydrochloric acid, sulfuric acid, formic acid or acetic acid, by reacting the obtained hydroxy compound of formula:

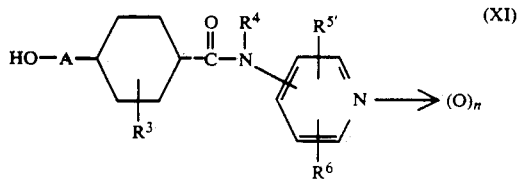

(XI)

wherein R⁵' is group other than hydroxy in R⁵ and other symbols are as defined above, with a halogenation reagent such as thionyl chloride, phosphorus oxychloride, phosphorous trichloride, phosphorus pentachloride or phosphorus tribromide, or with methanesulfonyl chloride or p-toluenesulfonyl chloride in the presence of a removing agent of hydrogen halide formed and reacting the corresponding reactive derivative of the alcohol compound with an amino compound of the formula:

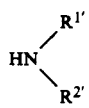

(XII)

wherein $R^{1'}$ is $C_{1-4}$ alkyl or phenylalkyl; $R^{2'}$ is $C_{1-4}$ alkyl, phenyl or phenylalkyl, or $R^{1'}$ and $R^{2'}$ together with the adjacent nitrogen atom form 5 to 6-membered cycle which may have oxygen atom, sulfur atom or optionally substituted nitrogen atom in the cycle.

The reaction can be carried out in the presence of a suitable base such as a hydroxide, a carbonate or a hydrogen-carbonate of an alkali metal and alkaline earth metal (e.g. sodium hydroxide, potassium carbonate, sodium hydrogencarbonate) or an organic base such as pyridine or triethylamine.

Further, isomers which is embraced in the compound of formula (I) of the present invention can be prepared by isolating from racemates in a conventional manner or using the corresponding isomers of the starting material.

The thus obtained compounds of the formula (I) can be separated and purified from the reaction mixture by a known method per se such as recrystallization or chromatography.

Moreover, the compounds of the formula (I) can be converted into pharmaceutically acceptable acid addition salts thereof according to a conventional manner. The acid for forming pharmaceutically acid addition salts can be suitably selected from an inorganic acid (e.g. hydrochloric acid, hydrobromic acid, sulfuric acid or phosphoric acid) or an orgainc acid (e.g. acetic acid, succinic acid, methanesulfonic acid, maleic acid or fumaric acid). These salts can be converted into the corresponding free base according to a conventional manner, for example, by reacting with an alkali such as sodium hydroxide or potassium hydroxide. Moreover, the compound of formula (I) can be converted into a tertiary ammonium salt thereof.

The preferable compounds are the compounds of formula (I) wherein $R^1$ and $R^2$ represent hydrogens, an optical isomer thereof and a pharmaceutically acceptable acid addition salt thereof.

More preferable compounds of the formula (I) include trans-4-aminomethyl-1-(4-pyridylcarbamoyl)cyclohexane, trans-4-aminomethyl-trans-1-methyl-1-(4-pyridylcarbamoyl)cyclohexane, trans-4-aminomethyl-cis-2-methyl-1-(4-pyridylcarbamoyl)cyclohexane, trans-4-(1-aminoethyl)-1-(4-pyridylcarbamoyl)cyclohexane, trans-4-aminomethyl-1-(2-pyridylcarbamoyl)cyclohexane, trans-4-aminomethyl-1-(3-pyridylcarbamoyl)cyclohexane, trans-4-aminomethyl-1[(3-hydroxy-2-pyridylcarbamoyl)]cyclohexane, trans-4-aminomethyl-1-(3-methyl-4-pyridylcarbamoyl)cyclohexane, 4-(trans-4-aminomethylcyclohexylcarboxamido)-2,6-dimethylpyridine-N-oxide, trans-4-aminomethyl-1-(2-methyl-4-pyridylcarbamoyl)cyclohexane, trans-4-(2-aminoethyl)-1-(4-pyridylcarbamoyl)cyclohexane, trans-4-(1-amino-1-methylethyl)-1-(4-pyridylcarbamoyl)cyclohexane, trans-4-(1-aminopropyl)-1-(4-pyridylcarbamoyl)cyclohexane, (+)-trans-4-(1-aminopropyl)-1-(4-pyridylcarbamoyl)cyclohexane, (−)-trans-4-(1-aminopropyl)-1-(4-pyridylcarbamoyl)cyclohexane, (+)-trans-4-(1-aminoethyl)-1-(4-pyridylcarbamoyl)cyclohexane, (−)-trans-4-(1-aminoethyl)-1-(4-pyridylcarbamoyl)cyclohexane and a pharmaceutically acceptable acid addition salt thereof.

The thus obtained compounds of formula (I) of the present invention and pharmaceutically acceptable acid addition salts thereof possess coronary and cerebral blood flow-increasing activities as a conventional calcium antagonist, and furthermore kidney blood flow-increasing activity which the conventional calcium antagonists do not exhibit. The blood flow-increasing effects are long-lasting, and blood pressure-lowering effects are high ceiling. Moreover, the compounds of the present invention are effective on angiospasms induced by not only a biogenic calcium agonist-like substance such as endotheline and also a calcium ionopher. It is known that the conventional calcium antagonists are not effective on the latter angiospasms.

Therefore, the compounds of the present invention are useful as antihypertensive agents and agents for the prevention and treatment of circulatory diseases such as coronary, cerebral or kidney.

The following pharmacological experiments explain the functions and effects of the compounds of the present invention in more detail.

The test compounds employed are as follows:

Test Compound A: Trans-4-aminomethyl-1-(4-pyridylcarbamoyl)cyclohexane 2 hydrochloride Test Compound B: Trans-4-aminomethyl-cis-2-methyl-1-(4-pyridylcarbamoyl)cyclohexane 2 hydrochloride 1 hydrate Test Compound C: Trans-4-(1-aminoethyl)-1-(4-pyridylcarbamoyl)cyclohexane 2 hydrochloride 1 hydrate

PHARMACOLOGICAL EXPERIMENT 1: ANTIHYPERTENSIVE EFFECT

Each of 30 mg/kg of test compounds dissolving in 0.5% of hydroxypropyl-methylcellurose was orally administered to groups of 3 to 5 male spontaneously hypertensive rats weighing 350–450 g. Three hours after the administration, the systolic blood pressure was measured by tail cuff method and antihypertensive effects are examined. The results are summarized in Table 1.

TABLE 1

| Test Compound | Maximum lowering value of systolic blood pressure (mmHg) |
|---|---|
| B | −44 |
| C | −52 |

PHARMACOLOGICAL EXPERIMENT 2: EFFECT ON CORONARY BLOOD FLOW

Groups of 2 to 3 adult mongrel dogs were anesthetized with the intraveneous administration of 30 mg/kg of body weight of sodium pentobarbital.

According to the method of Yago et. al. described in Folia Pharmacologica Japonica, vol. 57, p.380 (1961), the left coronary artery was perfused and its blood flow volume was measured. Test compound was injected into the coronary artery at a volume of 10–300 μg. The effects of test compound on coronary blood flow were expressed as $ED_{50}$ (μg), a dose required to increase the coronary blood flow by a half of the effects of the coronary-artery injection of 3 μg of nifedipine [Dimethyl 2,6-dimethyl-4-(2-nitrophenyl)-1,4-dihydropyridine-3,5-dicarboxylate]. The results are summarized in Table 2. Each of half-life (T ½, minute) was measured as the duration of effects.

TABLE 2

| Text compound | Effect of coronary blood flow | |
|---|---|---|
| | $Ed_{50}$ (μg, in artery) | T½ (min.) |
| A | 56 | 1.7 |
| B | 35 | 4.0 |
| C | 34 | 3.0 |

PHARMACOLOGICAL EXPERIMENT 3: EFFECT ON VERTEBRAL BLOOD FLOW

Groups of two adult mongrel dogs were anesthetized with the intraveneous administration of 25 mg/kg of body weight of sodium pentobarbital.

The right vertebral artery was perfused and the blood flow volume was measured. Test compound was injected in the vertebral artery. The percentage of maximum increase of blood flow by the injection of 100 μg of papaverine hydrochloride (1-[(3,4-dimethoxyphenyl)methyl]-6,7-dimethoxyisoquinoline hydrochloride) in vertebral artery was taken as 100%. The effects of test compound on vertebral artery were expressed as $ED_{100}$ (μg), a dose required to obtain 100% of the increase of blood flow. The results are summarized in the following Table 3. Each of half-life (T ½, minute) was measured as the duration of the effects.

TABLE 3

| Test Compound | Dose (μg) | Effect of vertebral blood flow | |
|---|---|---|---|
| | | $ED_{100}$ (μg) | T½ (min.) |
| A | 10–100 | 35 | 2.1 |
| B | 30–100 | 74 | 4.4 |
| C | 30–100 | 58 | 3.0 |

EXPERIMENT OF ACUTE TOXICITY

Each of test compounds of A, B and C was intraperitoneally administered to ddY strain mice. All mice survived at the intraperitoneal dose of 100 mg/kg for five days after administration.

When the compounds of the present invention are used as medicines, an effective amount of them can be usually admixed with pharmaceutically acceptable additives such as excipients, carriers and diluents and can be orally or parenterally administered in such a form of tablets, powders, granules, capsules, injections, ointments and suppositories. While the dosage may vary depending on the age, body weight, symptoms of the patients and the like, a daily dosage for a human adult is usually, in case of the oral administration, in the range from 5 to 500 mg, at single dose or several divided doses.

| Pharmaceutical Formulation Example | |
|---|---|
| The compound of the present invention | 10.0 mg |
| Lactose | 50.0 mg |
| Corn starch | 20.0 mg |
| Crystalline cellulose | 29.7 mg |
| Polyvinylpyrrolidone K30 | 5.0 mg |
| Talc | 5.0 mg |
| Magnesium stearate | 0.3 mg |
| | 120.0 mg |

The compound of the present invention, lactose, corn starch and crystalline cellulose were mixed and kneaded with a polyvinylpyrrolidone K30 binder. The kneaded mixture was subjected to sieve of 20 mesh to granulate. After drying at 50° C. for 2 hours, the granular products were subjected to sieve of 24 mesh and mixed with talc and magnesium stearate to prepare 120 mg tablets with a pounder of 7 mm diameter.

The present invention will be explained by the following examples in more detail, but these examples are not to be construed as limiting the present invention:

EXAMPLE 1

A mixture of 15.4 g of 4-aminopyridine, 20.6 g of triethylamine, 110 ml of dichloromethane and 165 ml of dimethylacetoamide was stirred under cooling in ice-water and a solution of 53 g of trans-4-benzyloxycarboxamidomethylcyclohexanecarbonyl chloride in 50 ml of dichloromethane was added dropwise thereto through a funnel at 5°–10° C. over one hour. After stirring at the same temperature for 3 hours, the mixture was stirred with heating at 50°–55° C. for 8 hours. After cooling, the reaction mixture was poured into water. The dichloromethane layer was washed with an aqueous solution of sodium hydrogencarbonate, dried and concentrated to give 68 g of the solid product. Ethyl acetate was added thereto and the obtained crystals were collected by filtration to give trans-4-benzyloxycarboxamidomethyl-1-(4-pyridylcarbamoyl)cyclohexane, melting at 178°–183° C. The obtained crystals were converted into the corresponding hydrochloride ½ hydrate, melting at 270° C. with decomposition.

EXAMPLE 2

After standing the mixture of 25 g of trans-4-benzyloxycarboxamidomethyl-1-(4pyridylcarbamoyl)cyclohexane and 500 g of a solution of 30% hydrobromic acid in acetic acid for 22 hours at room temperature, the precipitated crystals were collected by filtration and washed with ethanol and ether to give trans-4-aminomethyl-1-(4-pyridylcarbamoyl)cyclohexane 2 hydrobromide as crystals, melting at 267° C. with decomposition. The obtained crystals were dissolved in ice-water and alkalized with a solution of concentrated sodium hydroxide. The precipitated crystals were collected by filtration, washed with water and dried to give the corresponding base compound, melting at 148° C. To a solution of the thus obtained base compound in ethanol was added a solution of oxalic acid in ethanol. The precipitated crystals were collected by filtration and washed with ethanol and ether to give the corresponding 2 oxalate, melting at 221° C. with decomposition. The corresponding 2 hydrochloride melts at 292° C. with decomposition.

EXAMPLE 3

A mixture of 2.33 g of trans-4-aminomethyl-1-(4-pyridylcarbamoyl)cyclohexane, 15 ml of 99% formic acid and 18 ml of acetic anhydride was stirred and then an exothermic reaction occurred by 36° C. After refluxing for 10.5 hours, the resultant mixture was poured into ice-water and alkalized with potassium carbonate and an aqueous solution of concentrated sodium hydroxide. To the precipitated water substance was added chloroform. The obtained crystals were collected by filtration, washed with water and dried. The crystals were dissolved in ethanol and a solution of oxalic acid in ethanol added thereto. The precipitated crystals were collected by filtration and dried to give trans-4-formamidomethyl-1-(4-pyridylcarbamoyl)cyclohexane oxalate ½ hydrate, melting at 204°–207° C. with decomposition.

EXAMPLE 4

A mixture of 2.33 g of trans-4-aminomethyl-1-(4-pyridylcarbamoyl)cyclohexane, and 3.1 g of a mixture of 37% formalin and 85% formic acid was refluxed on an oil bath for 2.5 hours. After cooling, to the reaction mixture was added ice-water. The solution was alkalized with an aqueous solution of potassium carbonate and an aqueous solution of sodium hydroxide and subjected to extract with chloroform. After drying, the chloroform layer was concentrated to give 1.93 g of the solid product. The obtained solid product was dissolved in ethanol under heating and 25% ethanolic hydrochloric acid was added to precipitate the crystals. The crystals were collected by filtration and washed with ethanol and petroleum ether to give trans-4-dimethylaminomethyl-1-(4-pyridylcarbamoyl)cyclohexane 2 hydrochloride ½ hydrate, melting at 280°–283° C.

EXAMPLE 5

A mixture of 4.4 g of trans-4-aminomethyl-1-(4-pyridylcarbamoyl)cyclohexane, 2 g of benzaldehyde and 70 ml of toluene was poured into an eggplant type flask and refluxed to distill off a theoretical amount of water. After distilling fo 3.5 hours, to the residue was added an activated carbon and filtered off. The filtrate was concentrated, and to the solidified compound was added isopropyl ether and ethyl acetate. The obtained crystals were collected by filtration, washed with ethyl acetate and dried to give N-benzylidene-trans-(4-pyridylcarbamoyl)cyclohexylmethylamine, melting at 142°–145° C. To 5.6 g of the N-benzylidene compound was added 0.66 g of sodium borohydride in ethanol and treated by a conventional manner to give trans-4-benzylaminomethyl-1-(4-pyridylcarbamoyl)cyclohexane 2 hydrochloride ¾ hydrate, melting at 266°–268° C. with decomposition.

EXAMPLE 6

A mixture of 3 g of trans-4-aminomethyl-1-(4-pyridylcarbamoyl)cyclohexane 2 hydrobromide, 25 ml of methanol and 10 ml of acetone was stirred under ice-cooling and 3 g of sodium cyanoborohydride was added to the mixture. After stirring at 5°–10° C. for 3 hours, the reaction mixture was further stirred at room temperature for 3 hours. The reaction mixture was concentrated at 30° C. or below and the residue was poured into water. After extracting with butanol, the organic layer was concentrated and the residue was dissolved in methanol. To the methanol solution was added a solution of oxalic acid in methanol and the precipitated crystals were collected by filtration to give trans-4-isopropylaminomethyl-1-(4-pyridylcarbamoyl)cyclohexane 2 oxalate ½ hydrate, melting at 227° C. with decomposition.

EXAMPLE 7

To a mixture of 6 g of trans-4-aminomethyl-1-(4-pyridylcarbamoyl)cyclohexane 2 hydrobromide, 100 ml of pyridine and 100 ml of dimethylacetamide was added 3.5 g of nicotinoyl chloride hydrochloride under ice-cooling. After heating gradually, the reaction mixture was stirred at room temperature for 20 hours. The reaction mixture was concentrated and to the residue was added chloroform, and then the insoluble material was filtered off. After the solvent was concentrated, a solution of the viscous oily residue in isopropyl alcohol was separated by decantation and concentrated. Upon adding ethanol to the residue, the precipitated crystals were collected by filtration and recrystallized with a mixed solvent of methanol and ethanol to give trans-4-nicotinoylaminomethyl-1-(4-pyridylcarbamoyl)cyclohexane hydrobromide hydrochloride ½ hydrate, melting at 256° C. with decomposition.

EXAMPLE 8

A mixture of 3.95 g of trans-4-aminomethyl-1-(4-pyridylcarbamoyl)cyclohexane 2 hydrobromide, 1.6 g of cyclohexyl bromide, 4.5 g of potassium carbonate and 100 ml of dimethylformamide was stirred at 70° C. for 48 hours. The solvent was distilled off, to the residue was added ice-water followed by extracting with ethyl acetate. The organic layer was washed with water, dried and then concentrated. To the residue was added chloroform and the obtained crystals were collected by filtration. The crystals were dissolved in ethanol, added oxalic acid thereto and the solution was heated. Upon cooling, the fine crystals were precipitated, collected by filtration and further recrystallized with an aqueous ethanol to give trans-4-cyclohexylaminomethyl-1-(4-pyridylcarbamoyl)cyclohexane 2 oxalate, melting at 231° C. with decomposition.

EXAMPLE 9

To a mixture of 5.3 g of 4-aminopyridine, 13.7 g of triethylamine, 35 ml of dichloromethane and 50 ml of dimethylacetamide were added dropwise a solution of 20 g of trans-4-benzyloxycarboxamidocyclohexanecarbonyl chloride in 60 ml of dichloromethane under cooling with ice-water and stirring. After adding dropwise, the reaction mixture was stirred at 15°–20° C. for 2 hours and further, at 50°–55° C. for 4 hours. After completion of the reaction, the reaction mixture was cooled and poured into ice-water. The dichloromethane layer was washed with 5% of an aqueous solution of sodium hydrogen-carbonate and then water, dried and concentrated to give 19 g of trans-4-benzyloxycarboxamido-1-(4-pyridylcarbamoyl)cyclohexane as crystals, melting at 213°–215° C.

EXAMPLE 10

A solution of 19 g of trans-4-benzyloxycarboxamido-1-(4-pyridylcarbamoyl)-cyclohexane and 500 g of a solution of 25% hydrobromic acid in acetic acid was allowed to stand for 16 hours. The solution was poured into 2 l of ether and the precipitated crystals were collected by filtration. The obtained crystals were washed with ether and acetone and then washed with ethanol which was previously warmed at 50°–60° C. to give 15 g of trans-4-amino-1-(4-pyridylcarbamoyl)cyclohexane 2 hydrobromide, melting at 285° C. with decomposition.

EXAMPLE 11

To a suspension of 2.0 g of trans-4-(1-benzyloxycarboxamidoethyl)-1-(4-pyridylcarbamoyl)cyclohexane hydrochloride 1 hydrate in 100 ml of ethanol were added 1.5 ml of 10% hydrochloric acid and 4 g of 10% palladium-carbon (water content: 53.8%) and subjected to a catalytic reduction with hydrogen under atomospheric pressure at 15°-20° C. After verifying completion of the reaction with silica gel chromatography, the catalysts were filtered off and the filtrate was concentrated under reduced pressure to give a viscous oily substance. To the viscous oily substance was added a mixed solution of acetone and methanol to give 1.4 g of trans-4-(1-aminoethyl)-1-(4-pyridylcarbamoyl)cyclohexane 2 hydrochloride 1 hydrate, melting at 286°-287° C. with decomposition.

EXAMPLE 12

To a solution of 5.5 g of trans-4-benzyloxycarboxamidomethyl-cis-2-methyl-1-(4-pyridylcarbamoyl)cyclohexane hydrochloride 1 hydrate in 100 ml of ethanol were added 3.0 ml of concentrated hydrochloric acid and 3.0 g of 10% palladium-carbon, and subjected to a catalytic reduction with hydrogen under atmospheric pressure. After verifying completion of the reaction with thin layer chromatography, the insoluble material was filtered off. The filtrate was distilled off under reduced pressure, the obtained oily substance was dissolved in a 1:2 mixture of ethanol and acetone and the solution was allowed to stand under cooling overnight to give 3.0 g of trans-4-aminomethyl-cis-2-methyl-1-(4-pyridylcarbamoyl)cyclohexane 2 hydrochloride 1 hydrate in 74% yield, melting at 280°-282° C. with decomposition. The corresponding 1¾ oxalate melts at 222° C. with decomposition.

EXAMPLE 13

Trans-4-(1-benzylcarboxamidopropyl)-1-cyclohexanecarboxylic acid was subjected to optical resolution with L-(−)-α-phenethylamine to give (+)-trans-4-(1-benzylcarboxamidopropyl)-1-cyclohexanecarboxylic acid, melting at 140° C.

Optical rotation: $[\alpha]_D^{23} = +2.4°$ (c=1, ethanol).

The obtained (+)-carboxylic acid compound was converted into the corresponding acid chloride by using a conventional manner. The obtained acid chloride compound was condensed with 4-aminopyridine and treated in the similar manner as described in the Example 1 to give (+)-trans-4-(1-benzyloxycarboxamidopropyl)-1-(4-pyridylcarbamoyl)cyclohexane hydrochloride 1 hydrate, melting at 210° C.

Optical rotation: $[\alpha]_D^{23} = +18.7°$ (c=1, ethanol).

EXAMPLE 14

By the use of trans-4-(1-benzyloxycarboxamidopropyl)-1-cyclohexanecarboxylic acid and D-(+)-α-phenethylamine, the optical resolution was similarly carried out as Example 13 to give (−)-trans-4-(1-benzyloxycarboxamidopropyl)-1-cyclohexanecarboxylic acid, melting at 142° C.

Optical rotation: $[\alpha]_D^{23} = -22.6°$ (c=1, ethanol). The obtained (−)-carboxylic acid compound was converted into the corresponding acid chloride. The obtained acid chloride compound was condensed with 4-aminopyridine and treated in the similar manner as described in the Example 1 to give (−)-trans-4-(1-benzyloxycarboxamidopropyl)-1-(4-pyridylcarbamoyl)cyclohexane hydrochloride 1 hydrate, melting at 208° C.

Optical rotation: $[\alpha]_D^{23} = -18.5°$ (c=1, ethanol).

EXAMPLE 15

(+)-Trans-4-(1-benzyloxycarboxamidopropyl)-1-(4-pyridylcarbamoyl)cyclohexane hydrochloride 1 hydrate was subjected to a catalytic reduction with hydrogen under atmospheric pressure and treated in the similar manner as described in the Example 11 to give (+)-trans-4-(1-aminopropyl)-1-(4-pyridylcarbamoyl)cyclohexane 2 hydrochloride 1 hydrate, melting at 238° C. with decomposition.

Optical rotation: $[\alpha]_D^{25} = +4.6°$ (c=1, ethanol).

EXAMPLE 16

(−)-Trans-4-(1-benzyloxycarboxamidopropyl)-1-(4-pyridylcarbamoyl)cyclohexane hydrochloride 1 hydrate was subjected to a catalytic reduction with hydrogen under atmospheric pressure and treated in the similar manner as described in the Example 11 to give (−)-trans-4-(1-aminopropyl)-1-(4-pyridylcarbamoyl)cyclohexane 2 hydrochloride 1 hydrate, melting at 235° C. with decomposition.

Optical rotation: $[\alpha]_D^{25} = -4.4°$ (c=1, ethanol).

EXAMPLE 17

Trans-4-(1-benzyloxycarboxamidoethyl)-1-cyclohexanecarboxylic acid was subjected to optical resolution with L-(−)-α-phenethylamine to give (−)-trans-4-(1-benzyloxycarboxamidoethyl)-1-cyclohexanecarboxylic acid.

Optical rotation: $[\alpha]_D^{23} = -4.7°$ (c=0.1, ethanol).

The obtained (−)-carboxylic acid compound was converted into the corresponding acid chloride by using a conventional manner. The obtained acid chloride compound was condensed with 4-aminopyridine and treated in the similar manner as described in the Example 1 to give (−)-trans-4-(1-benzyloxycarboxamidoethyl)-1-(4-pyridylcarbamoyl)cyclohexane, melting at 192° C.

Optical rotation: $[\alpha]_D^{23} = -8.4°$ (c=0.4, ethanol).

EXAMPLE 18

Trans-4-(1-benzyloxycarboxamidoethyl)-1-cyclohexanecarboxylic acid was subjected to optical resolution with D-(+)-α-phenethylamine to give (+)-trans-4-(1-benzyloxycarboxamidoethyl)-1-cyclohexanecarboxylic acid.

Optical rotation: $[\alpha]_D^{23} = +4.5°$ (c=0.5, ethanol).

The obtained (+)-carboxylic acid compound was converted into the corresponding acid chloride by using a conventional manner. The obtained acid chloride compound was condensed with 4-aminopyridine and treated in a similar manner as described in the Example 1 to give (+)-trans-4-(1-benzyloxycarboxamidoethyl)-1-(4-pyridylcarbamoyl)cyclohexane, melting at 190° C.

Optical rotation: $[\alpha]_D^{23} = +8.1°$ (c=1, ethanol).

EXAMPLE 19

(+)-Trans-4-(1-benzyloxycarboxycarboxamidoethyl)-1-(4-pyridylcarbamoyl)cyclohexane was subjected to a catalytic reduction with hydrogen under atmospheric pressure and treated in the similar manner as described in the Example 11 to give (+)-trans-4-(1- aminoethyl)-1-(4-pyridylcarbamoyl)cyclohexane 2 hydrochloride ½ hydrate, melting at 276° C. with decomposition.

Optical rotation: $[\alpha]_D^{23} = +4.6°$ (c=1, methanol).

EXAMPLE 20

(−)-Trans-4-(1-benzyloxycarboxamidoethyl)-1-(4-pyridylcarbamoyl)cyclohexane was subjected to a catalytic reduction with hydrogen under atmospheric pressure and treated in the similar manner as described in the Example 11 to give (−)-trans-4-(1-aminoethyl)-1-(4-pyridylcarbamoyl)cyclohexane 2 hydrochloride ½ hydrate, melting at 279° C. with decomposition.

Optical rotation: $[\alpha]_D^{23} = -4.9°$ (c=0.7, methanol).

The following compounds can be prepared in a similar manner mentioned in the above examples.

(1) Trans-4-(4-chlorobenzoyl)aminomethyl-1-(4-pyridylcarbamoyl)cyclohexane oxalate ½ hydrate, melting at 204° C. with decomposition (2) Trans-4-aminomethyl-1-(2-pyridylcarbamoyl)cyclohexane 2 hydrochloride, melting at 245° C. with decomposition (3) Trans-4-benzyloxycarboxamidomethyl-1-(2-pyridylcarbamoyl)cyclohexane, melting at 133°–137° C.

(4) Trans-4-methylaminomethyl-1-(4-pyridylcarbamoyl)cyclohexane 2 oxalate, melting at 211°–212° C. with decomposition (5) Trans-4-(2-phenylethyl)aminomethyl-1-(4-pyridylcarbamoyl)cyclohexane (6) Trans-4-(N-acetyl-N-methylamino)methyl-1-(4-pyridylcarbamoyl)cyclohexane (7) Trans-4-cyclohexylcarbonylaminomethyl-1-(4-pyridylcarbamoyl)cyclohexane (8) Trans-4-hexylaminomethyl-1-(4-pyridylcarbamoyl)cyclohexane (9) Trans-4-diethylaminomethyl-1-(4-pyridylcarbamoyl)cyclohexane

(10) Trans-4-(4-benzyl-1-piperadinyl)methyl-1-(4-pyridylcarbamoyl)cyclohexane

(11) Trans-4-(1-piperadinyl)methyl-1-(4-pyridylcarbamoyl)cyclohexane

(12) Trans-4-morpholinomethyl-1-(4-pyridylcarbamoyl)cyclohexane

(13) Trans-4-thiomorpholinomethyl-1-(4-pyridylcarbamoyl)cyclohexane

(14) Trans-4-guanidinomethyl-1-(4-pyridylcarbamoyl)cyclohexane

(15) Trans-4-(1-benzyl-4-piperidinyl)aminomethyl-1-(4-pyridylcarbamoyl)cyclohexane

(16) Trans-4-(2-nitrophenyl)aminomethyl-1-(4-pyridylcarbamoyl)cyclohexane

(17) Trans-4-(2-aminophenyl)aminomethyl-1-(4-pyridylcarbamoyl)cyclohexane

(18) Trans-4-butylaminomethyl-1-(4-pyridylcarbamoyl)cyclohexane

(19) Trans-4-cyclopentylaminomethyl-1-(4-pyridylcarbamoyl)cyclohexane

(20) Trans-4-(N-benzyl-N-methylamino)methyl-1-(4-pyridylcarbamoyl)cyclohexane 2 oxalate 1 hydrate, melting at 206°–208° C. with decomposition

(21) Trans-4-(4-methylcyclohexyl)aminomethyl-1-(4-pyridylcarbamoyl)cyclohexane

(22) Trans-4-(2-methylcyclohexyl)aminomethyl-1-(4-pyridylcarbamoyl)cyclohexane

(23) Trans-4-(1-benzyl-4-piperidylidene)aminomethyl-1-(4-pyridylcarbamoyl)cyclohexane

(24) Trans-4-(4-piperidyl)aminomethyl-1-(4-pyridylcarbamoyl)cyclohexane

(25) Trans-4-(4-fluorobenzoyl)aminomethyl-1-(4-pyridylcarbamoyl)cyclohexane

(26) Trans-4-[2-(3,4-dimethoxyphenyl)-1-methylethyl]aminomethyl-1-(4-pyridylcarbamoyl)cyclohexane

(27) Trans-4-(N-benzyl-N-ethylamino)methyl-1-(4-pyridylcarbamoyl)cyclohexane

(28) Trans-4-ethylaminomethyl-1-(4-pyridylcarbamoyl)cyclohexane

(29) Trans-4-aminomethyl-1-(3-pyridylcarbamoyl)cyclohexane 2 hydrochloride, melting at 250° C. with decomposition

(30) Trans-4-aminomethyl-1-[(3-benzyloxy-2-pyridyl)carbamoyl]cyclohexane

(31) Trans-4-aminomethyl-1-[(3-hydroxy-2-pyridyl)carbamoyl]cyclohexane 2 hydrochloride 1 hydrate, melting at 195°–200° C.

(32) Trans-4-benzyloxycarboxamidomethyl-1-(3-pyridylcarbamoyl)cyclohexane, melting at 180°–183° C.

(33) Trans-4-benzyloxycarboxamidomethyl-1-[(3-benzyloxy-2-pyridyl)carbamoyl]cyclohexane, melting at 192°–195° C.

(34) Trans-4-phthalimidomethyl-1-(4-pyridylcarbamoyl)cyclohexane hydrochloride 1 hydrate, melting at 246°–248° C.

(35) Trans-4-benzyloxycarboxamidomethyl-1-(3-methyl-4-pyridylcarbamoyl)cyclohexane, melting at 185°–190° C. with decomposition

(36) Trans-4-aminomethyl-1-(3-methyl-4-pyridylcarbamoyl)cyclohexane 2 hydrochloride, melting at 285°–287° C. with decomposition

(37) 4-(Trans-4-benzyloxycarboxamidomethylcyclohexylcarbonyl)amino-2,6-dimethylpyridine-N-oxide, melting at 180°–183° C. with decomposition

(38) 4-(Trans-4-aminomethylcyclohexylcarbonyl)amino-2,6-dimethylpyridine-N-oxide 2 hydrobromide, melting at 278°–280° C. with decomposition

(39) Trans-4-aminomethyl-1-(2-methyl-4-pyridylcarbamoyl)cyclohexane 2 hydrochloride 1 hydrate, melting at 265°–268° C. with decomposition

(40) Trans-4-(1-benzyloxycarboxamidoethyl)-1-(4-pyridylcarbamoyl)cyclohexane 1 hydrochloride 1 hydrate, melting at 198°–200° C. with decomposition

(41) Trans-4-aminomethyl-trans-2-methyl-1-(4-pyridylcarbamoyl)cyclohexane

(42) Trans-4-aminomethyl-trans-3-methyl-1-(4-pyridylcarbamoyl)cyclohexane

(43) Trans-4-aminomethyl-cis-3-methyl-1-(4-pyridylcarbamoyl)cyclohexane

(44) Trans-4-aminomethyl-cis-4-methyl-1-(4-pyridylcarbamoyl)cyclohexane

(45) Trans-4-(1-amino-1-methylethyl)-1-(4-pyridylcarbamoyl)cyclohexane 2 hydrochloride, melting at 310° C. with decomposition Trans-4-(1-amino-1-methylethyl)-1-(4-pyridylcarbamoyl)cyclohexane 2 hydrochloride 2 hydrate, melting at 313°–315° C. with decomposition Trans-4-(1-amino-1-methylethyl)-1-(4-pyridylcarbamoyl)cyclohexane 2 hydrobromide, melting at 271° C. with decomposition

(46) Trans-4-(2-aminoethyl)-1-(4-pyridylcarbamoyl)cyclohexane 2 hydrochloride, melting at 260°–263° C. with decomposition

(47) Trans-4-aminomethyl-cis-2-ethyl-1-(4-pyridylcarbamoyl)cyclohexane

(48) Trans-4-(2-aminopropyl)-1-(4-pyridylcarbamoyl)cyclohexane

(49) Trans-4-(2-amino-1-methylethyl)-1-(4-pyridylcarbamoyl)cyclohexane fumarate ½ hydrate, melting at 185°–187° C. with decomposition

(50) Trans-4-(1-aminopropyl)-1-(4-pyridylcarbamoyl)cyclohexane 2 hydrochloride 1 hydrate, melting at 286°–288° C. with decomposition

(51) Trans-4-amino-cis-2-methyl-1-(4-pyridylcarbamoyl)cyclohexane

(52) Trans-4-aminomethyl-trans-1-methyl-1-(4-pyridylcarbamoyl)cyclohexane 2 hydrochloride 2 hydrate, melting at 165°–170° C. with decomposition

(53) Trans-4-benzylaminomethyl-cis-2-methyl-1-(4-pyridylcarbamoyl)cyclohexane 2 oxalate 3/2 hydrate, melting at 190° C. with decomposition

(54) Trans-4-(1-benzyloxycarboxamido-1-methylethyl)-1-(4-pyridylcarbamoyl)cyclohexane hydrochloride, melting at 210° C. with decomposition Trans-4-(1-benzyloxycarboxamido-1-methylethyl)-1-(4-pyridylcarbamoyl)cyclohexane ½ hydrate, melting at 154°–155° C.

(55) Trans-4-benzyloxycarboxamidomethyl-1-(N-methyl-4-pyridylcarbamoyl)cyclohexane oxalate 1 hydrate, melting at 132° C. with decomposition

(56) Trans-4-(1-acetamido-1-methylethyl)-1-(4-pyridylcarbamoyl)cyclohexane ½ hydrate, melting at 250°–253° C.

While the present invention has been in detail explained in the specification including working examples, can be changed and modified in various ways within the spirit and scope of the present invention.

What is claimed is:

1. A trans-4-amino(alkyl)-1-pyridylcarbamoylcyclohexane compound of the formula:

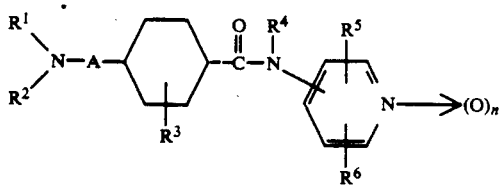

wherein $R^1$ and $R^2$ are the same or different, and respectively represent:

hydrogen, $C_{1-10}$ alkyl, $C_{2-5}$ alkanoyl, formyl, $C_{1-4}$ alkoxy-carbonyl, amidino, $C_{3-7}$ cycloalkyl, $C_{3-7}$ cycloalkyl-carbonyl, unsubstituted or substituted phenyl, phenylalkyl, benzoyl, naphthoyl, phenylalkoxy-carbonyl, pyridylcarbonyl or piperidyl, wherein the substituent is selected from the group consisting of halogen, $C_{1-4}$ alkyl, $C_{1-4}$ alkoxy, phenylalkyl, nitro or amino, $R^1$ and $R^2$ together form unsubstituted or substituted benzylidene, pyrrolidylidene or piperidylidene, wherein the substituent is selected from the group consisting of halogen, $C_{1-4}$ alkyl, $C_{1-4}$ alkoxy, phenylalkyl, nitro or amino, or $R^1$ or $R^2$ together with the adjacent nitrogen atom form pyrrolidinyl, piperidino, piperazinyl, morpholino, thiomorpholino or phthalimido, $R^3$ represents hydrogen or $C_{1-4}$ alkyl, $R^4$ represents a hydrogen or $C_{1-4}$ alkyl, $R^5$ represents hydrogen, hydroxy, $C_{1-4}$ alkyl or phenylalkoxy, $R^6$ represents hydrogen or $C_{1-4}$ alkyl, A represents single bond, $C_{1-5}$ straight chain alkylene, or alkylene which is substituted by $C_{1-4}$ alkyl and n represents 0 to 1, and an optical isomer thereof or a pharmaceutically acceptable acid addition salt thereof.

2. The compound of claim 1, wherein $R^1$ and $R^2$ represent hydrogens, an optical isomer thereof or a pharmaceutically acceptable acid addition salt thereof.

3. The compound of claim 1, which is selected from the group consisting of trans-4-aminomethyl-1-(4-pyridylcarbomoyl)cyclohexane, trans-4-aminomethyl-trans-1-methyl-1-(4-pyridylcarbamoyl)cyclohexane, trans-4-aminomethyl-cis-2-methyl-1-(4-pyridylcarbamoyl)cyclohexane, trans-4-aminomethyl-1-(2-pyridylcarbamoyl)cyclohexane, trans-4-aminomethyl-1-(3-pyridylcarbamoyl)cyclohexane, trans-4-aminomethyl-1[(3-hydroxy-2-pyridylcarbamoyl)]cyclohexane, trans-4-aminomethyl-1-(3-methyl-4pyridylcarbamoyl)cyclohexane, 4-(trans-4-aminomethylcyclohexylcarboxamido)-2,6-dimethyl-pyridine-N-oxide, trans-4-aminomethyl-1-(2-methyl-4-pyridylcarbamoyl)cyclohexane, trans-4-(2-aminoethyl)-1-(4-pyridylcarbamoyl)cyclohexane, trans-4-(1-amino-1-methylethyl)-1-(4-pyridylcarbamoyl)cyclohexane, trans-4-(1-aminopropyl)-1-(4-pyridylcarbamoyl)cyclohexane, or a pharmaceutically acceptable acid addition salt thereof.

4. A pharmaceutical composition for the prevention or treatment of circulatory diseases comprising an effective amount of the compound of any one of claims 1 to 3 and a pharmaceutically acceptable additive.

5. The compound according to claim 3 which is (+)trans-4-(1-aminopropyl)-1-(4-pyridylcarbamoyl)cyclohexane.

6. The compound according to claim 3 which is (−)trans-4-(1-aminopropyl)-1-(4-pyridylcarbamoyl)cyclohexane.

7. The compound according to claim 3 which is (+)trans-4-(1-aminoethyl)-1-(4-pyridylcarbamoyl)cyclohexane.

8. The compound according to claim 3 which is (−)trans-4-(1-aminoethyl)-1-(4-pyridylcarbamoyl)cyclohexane.

* * * * *